United States Patent [19]

Thomas et al.

[11] Patent Number: 5,391,792
[45] Date of Patent: Feb. 21, 1995

[54] GERMANIUM COMPOUNDS AND THEIR USE AS A BIOCOMPATIBLE OIL

[75] Inventors: Christian Thomas, Paris; Paolo Fossi, Elancourt; Elisabeth Perrier, Maurepas; Pierre Mazerolles, Castanet, all of France

[73] Assignee: Metaleurop S.A., Fontenay-Sous-Bois, France

[21] Appl. No.: 189,103

[22] Filed: Jan. 31, 1994

Related U.S. Application Data

[63] Continuation-in-part of Ser. No. 30,363, Mar. 18, 1993, abandoned.

[30] Foreign Application Priority Data

Jul. 19, 1991 [FR] France .................. 91 09157

[51] Int. Cl.$^6$ ............................ C07F 7/30
[52] U.S. Cl. .................................. 556/83
[58] Field of Search ........................ 556/83

[56] References Cited

U.S. PATENT DOCUMENTS

| | | | |
|---|---|---|---|
| 2,416,360 | 2/1947 | Trautman et al. | 252/49.6 |
| 2,451,871 | 10/1948 | Rochour | 260/429 |
| 2,506,386 | 5/1950 | Rochour | 260/429 |
| 3,393,215 | 7/1968 | Moedritzer et al. | 260/429 |

FOREIGN PATENT DOCUMENTS 1190462 4/1965 Germany .

OTHER PUBLICATIONS

Chemical Abstracts, vol. 83, Abstract No. 153583f (1975).
Bulletin of the Chemical Society of Japan, vol. 64, No. 4, Apr. 1991.

*Primary Examiner*—José G. Dees
*Assistant Examiner*—Porfirio Nazario-Gonzalez

[57] ABSTRACT

The present invention is a germanium compound having the following general formula I:

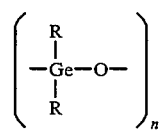

in which n is a positive integer less than 50 when the general formula is linear and is between 3 and 50 when the general formula is cyclic, and preferably between 3 and 6, and the R radicals, which are identical or different, are chosen independently from hydrocarbyl radicals, or, the R radicals form a hydrocarbon chain optionally containing one or two heteroatoms, optionally substituted by one or more $C_1$–$C_3$ alkyl radicals, which are optionally unsaturated, the compound of general formula I being, when it is linear, terminated by two radicals $R_3Ge-$ and $R_3Ge-O-$ respectively, provided that the different R radicals cannot simultaneously correspond to a methyl radical and when the general formula I is cyclic, the two radicals attach to the same germanium atom, cannot correspond to a divalent chain of the formula:

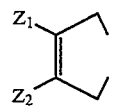

$Z_1$ and $Z_2$ being chosen from methyl radicals or hydrogen atoms.

14 Claims, No Drawings

GERMANIUM COMPOUNDS AND THEIR USE AS A BIOCOMPATIBLE OIL

This is a continuation in part of application Ser. No. 08/030,363, filed Mar. 18, 1993, now abandoned.

The subject of the invention is new germanium compounds or germoxanes and their use as a biocompatible oil. Its subject is also a process for preparing them.

Materials which can be used as biocompatible oils are already known. They are mainly silicones, of which the most representative family corresponds to the formula $((CH_3)_2SiO)_n$, where n designates the number of monomeric units and can reach very high values, ranging up to several tens of thousands of units.

Silicone oils have viscosity and biocompatability characteristics which render them suitable for the use indicated.

However, in certain applications, especially when they are used as fluid for filling prostheses intended to remain in the human body for a long period, they exhibit insufficient biodegradability. It has indeed been observed that the filling fluid tends to exude through the membrane separating it from the body due to the lack of flow resistance. However, when this filling fluid is a silicone oil, the oil tends to accumulate in the reticuloendothelial system, causing autoimmune diseases (rheumatoid arthritis) cf.: Chirurgie, 1988, 114, p. 538–544 and Ann. Chir. Plast. Esthét., 1986, 31, 3, p. 268–271.

The invention is precisely intended to overcome this disadvantage.

Furthermore, polymers obtained from methylgermanium chloride which can be used as lubricant for certain applications are known via patent U.S. Pat. No. 2,451,871. However, the rheological properties of these polymers do not make it possible to meet in a satisfactory manner the objectives set by the present invention.

The inventors have observed that germanium compounds, most of which are new, have characteristics which are compatible with a use as biocompatible oil (especially good rheological characteristics), while having, on the other hand, a satisfactory biodegradability.

Accordingly, the subject of the invention is firstly germanium compounds or germoxanes corresponding to the following general formula:

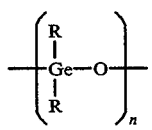
(I)

in which: n is a positive integer less than 50 when (I) is linear and between 3 and 50 when it is cyclic, preferably between 3 and 6, the R radicals, which are identical or different, are chosen independently from hydrocarbyl radicals, or alternatively, the R radicals attached to the same germanium atom together form a hydrocarbon chain optionally containing one or two heteroatoms, optionally substituted by one or more ($C_1$-$C_3$)alkyl radicals, optionally unsaturated, the compound (I) being, when it is linear, terminated by two radicals $(R)_3Ge$— and $(R)_3Ge$—O— respectively, provided that the different R radicals cannot simultaneously correspond to a methyl radical and when (I) is cyclic, the two R radicals attached to the same germanium atom cannot correspond to a divalent chain of formula:

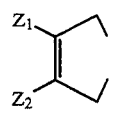

$Z_1$, $Z_2$ being chosen from methyl radicals or the hydrogen atom.

The compounds are moreover such that the said compounds or a mixture of two or more of the said compounds have a viscosity appropriate for a use as biocompatible oil.

The good biodegradability of this type of compounds probably results from the observation according to which the Ge—O bond is thermodynamically weaker than the Si—O bond, which therefore favors its disruption. This higher lability of the Ge—O bond and [sic] described in the literature, for example the Handbook of Chemistry and Physics.

In the context of the present invention, the word hydrocarbyl should be understood to include the groups containing carbon and hydrogen. The hydrocarbyl groups have a carbon atom directly attached to the rest of the molecule and have a mainly hydrocarbon character. These groups are often called hydrocarbon-based groups. These groups contain the following:

(1) hydrocarbon groups, that is to say aliphatic groups (for example alkyl or alkenyl), alicyclic groups (for example cycloalkyl or cycloalkenyl), aromatic groups, aromatic groups substituted by aliphatic and alicyclic groups. Such groups are known to persons skilled in the art: examples comprise methyl, ethyl, butyl, hexyl, octyl, decyl, dodecyl, tetradecyl, octadecyl, eicosyl, cyclohexyl and phenyl groups (all the isomers being included).

(2) Substituted hydrocarbon groups, that is to say groups containing nonhydrocarbyl substituents which, in the context of the present invention, do not alter the mainly hydrocarbon character of the group. Appropriate substituents comprise halo substituents.

(3) Hetero groups, that is to say groups which, although having a mainly hydrocarbon character in the context of the present invention, contain atoms, other than carbon, present in a chain or a ring which are moreover composed of carbon atoms. Appropriate heteroatoms are evident for persons skilled in the art and comprise, for example, those of nitrogen, oxygen and sulfur.

In general, there will not be more than about three substituents or heteroatoms, preferably not more than one, per 10 carbon atoms in the hydrocarbon-based group. In a particularly preferred manner, the hydrocarbon-based groups are purely hydrocarbon groups.

According to an advantageous variant, the germoxanes correspond to the formula:

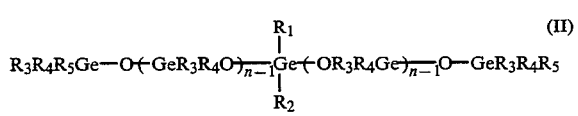
(II)

in which n is an integer between 1 and 50, preferably 3 and 6, $R_1$, $R_2$, $R_3$, $R_4$, $R_5$, independently of each other, have one of the meanings of R.

According to another advantageous characteristic of the compounds conforming to the invention, they have substituents with a relatively low molecular mass, by analogy with silicon compounds which can be used in the same applications.

Preferably, the substituents $R_1$ to $R_5$ are chosen from the radicals $(C_1-C_6)$alkyl, $(C_2-C_6)$alkenyl, $(C_3-C_6)$cycloalkyl which is optionally substituted by one or two $(C_1-C_3)$alkyl radicals, phenyl which is optionally substituted by one or two $(C_1-C_3)$alkyl radicals or alternatively $R_1$, $R_2$ and/or $R_3$, $R_4$ together form a divalent chain containing 4 or 5 carbon atoms, optionally one ethylenic unsaturation, optionally one to three $(C_1-C_3)$alkyl substituents.

More preferably, $R_1$, $R_2$ are a methyl radical.

According to another advantageous variant, taken in combination with one of the two preceding variants or both, $R_3$, $R_4$ are chosen from optionally substituted phenyl radicals or together form a divalent chain —C—C=C—C— which is optionally substituted by 1 or 2 methyl or ethyl substituents, but on two different carbons and/or $R_5$ is an n-propyl or n-butyl radical.

Unexpectedly, according to a preferred embodiment, it was found that the compounds of formula II below displayed a better stabilizing effect on the molecule avoiding the intramolecular rearrangement in the long run. Those Germoxanes are of formula:

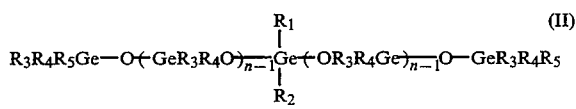
(II)

wherein n is an integer between 1 and 50 $R_1$, $R_2$ are chosen among the phenyl optionally substituted by one to five $(C_1-C_3)$ alkyl radicals, $R_3$, $R_4$, $R_5$ are chosen among the radicals $(C_1-{}^{12})$ alkyl, $(C_2-C_{12})$ alkenyl, $(C_3-C_6)$ cycloalkyl which is optionally substituted by one or two $(C_1-C_3)$ alkyl radicals. Preferably n is an integer lower than 6. Preferably $R_1$, $R_2$ are chosen among the phenyl trisubstituted and advantageously phenyl-o, -o, -p trisubstituted and more advantageously. -o, -o, -p trimethyl substituted. Preferably $R_3$, $R_4$, $R_5$ are chosen among the $(C_1-C_6)$ alkyl radicals, $(C_2-C_6)$ alkenyle radicals and more advantageously $R_3$, $R_4$, $R_5$ are chosen among the methyl or ethyl radicals.

Instead of the linear formula II, the germoxanes may also, in another preferred embodiment, correspond to the formula:

$$(R_4R_3GeO)_n \qquad (III)$$

in which n is between 3 and 6, $R_3$, $R_4$, which are identical or different, have one of the meanings indicated above, including with the preferred variants.

The compounds according to the invention can be prepared by organic synthesis comprising several steps, under conditions comparable with those used for the preparation of silicone oils. The synthesis conditions vary according to the viscosity and the geometry which are desired for the final compound.

The invention also relates to a process for preparing the compounds of formula I or II or III, characterized in that a germanium hydrocarbyl dihalide of formula $(R)_2GeX_2$, X being a halogen atom, R having one of the meanings indicated above, is hydrolyzed, then, optionally, in that the cyclic compound is reacted with a hydrocarbyllithium (RLi) to give a compound of formula:

$$(R)_3GeOLi$$

which is brought into contact with a germanium hydrocarbyl dihalide of formula $(R)_2GeY_2$, Y being a halogen atom, R having one of the meanings indicated above, or in that the said cyclic compound is opened by reaction with a hydrocarbyllithium (RLi) and then brought into contact with the germanium hydrocarbyl dihalide of the form $(R)_2GeY_2$.

The process according to the invention may also be schematically represented according to the following reaction scheme:

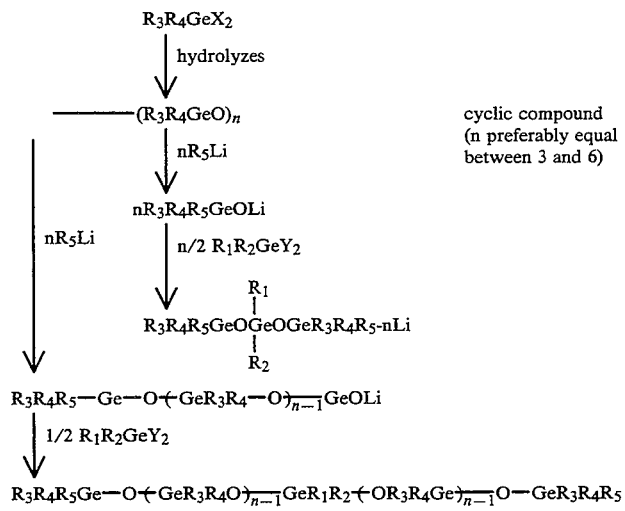

The subject of the invention is also the use of the compounds conforming to the invention of formula I:

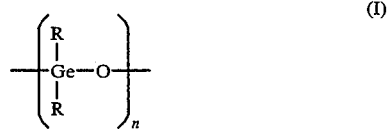
(I)

in which: n is a positive integer less than 50 when (I) is linear and between 3 and 50 when it is cyclic, preferably between 3 and 6, the R radicals, which are identical or different, are chosen independently from hydrocarbyl radicals, or alternatively, the R radicals attached to the same germanium atom together form a hydrocarbon chain optionally containing one or two heteroatoms, optionally substituted by one or more ($C_1$–$C_3$)alkyl radicals, optionally unsaturated, the compound (I) being, when it is linear, terminated by two radicals (R)$_3$Ge— and (R)$_3$Ge—O— respectively, provided that the different R radicals cannot simultaneously correspond to a methyl radical, in the field of human or animal biology, in all the applications where it is necessary to have biocompatible oils.

In all the applications envisaged, one or more of the compounds conforming to the invention can be used simultaneously. In the case where several compounds are used simultaneously, it is their mixture which has the required characteristics, especially in terms of viscosity.

The uses are in particular as fluid for devices for use inside the human or animal body, for example as fluids for lubricating syringes.

The uses are especially as fluid for filling prostheses for which they have an advantage in terms of biodegradability compared with known products, especially in the case of mammary prostheses.

Finally, the subject of the invention is a soft prosthesis characterized in that it comprises, as filling fluid, at least one compound conforming to the invention.

The invention is illustrated by the following example:

Preparation of the compound of formula

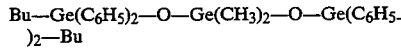
Bu—Ge($C_6H_5$)$_2$—O—Ge($CH_3$)$_2$—O—Ge($C_6H_5$)$_2$—Bu 1.5 g (2.06×10$^{-3}$ mole) of [$\phi_2$GeO]$_3$, in 40 ml of anhydrous ether, are introduced into a 150-ml two-necked Erlenmeyer flask with ground joints (purged with argon), provided with a condenser and a stopper with a flange. 3.9 ml (6.24×10$^{-3}$ mole) of a 1.6M solution of BuLi are introduced, with stirring, by means of a syringe.

After addition, the mixture is heated for one hour at the reflux temperature of the ether. 0.53 g (3.09×10$^{-3}$ mole) of Me$_2$GeCl$_2$ is rapidly introduced. The reflux and the stirring are maintained for one hour.

The precipitate (LiCl) is separated from the mixture by filtration. The ether is evaporated and 1.7 g of crude product are recovered.

The predominant product is the expected product. It is purified over a column.

The product is then introduced into an envelope for mammary prosthesis.

Preparation of the compound of formula

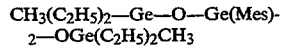
CH$_3$(C$_2$H$_5$)$_2$—Ge—O—Ge(Mes)$_2$—OGe(C$_2$H$_5$)$_2$CH$_3$ wherein the connotation Mes means O—,O—, p—C$_6$H$_2$(CH$_3$)$_3$ 64,46 g (0,146 mole) of [(C$_2$H$_5$)$_2$GeO]$_3$ in 350 ml of anhydrous ether is introduced into a reaction vessel. Under stirring at 0° C. is then introduced 275 ml (0,44 mole) of a 1,6M solution in ether of CH$_3$Li. After addition, the mixture is heated for one hour and an half at the reflux temperature of the ether under stirring. Then 82,8 g (0,217 mole) of (Mes)$_2$GeCl$_2$ diluted in about 750 ml of anhydrous tetrahydrofuran is added at ambient temperature. The mixture is heated at the reflux temperature of the diethylic ether which is distillated and the temperature is maintained during 7 days at the reflux temperature of the tetrahydrofuran. When the reaction is over, the tetrahydrofuran is evaporated, the precipitate of LiCl eliminated by centrifugation. A thick and orange liquid is recovered which is distillated (180°–190° C./0,1 mm Hg)

Yield (in Ge): 58,5%.

We claim:

1. A germoxane of the formula:

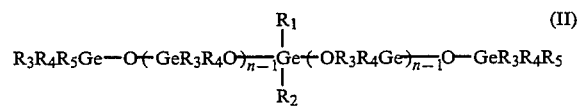

wherein n is an integer between 1 and 50

$R_1$, $R_2$ are a methyl radical $R_3$, $R_4$ are chosen among the phenyl optionally substituted by one to five ($C_1$–$C_3$) alkyl radicals or together form a divalent chain containing 4 or 5 carbon atoms, optionally one ethylene unsaturation, optionally one to three ($C_1$–$C_3$) alkyl substituents, $R_5$ is chosen from the radicals ($C_1$–$C_6$) alkyl, ($C_2$–$C_6$) alkenyl, ($C_3$–$C_6$) cycloalkyl which is optionally substituted by one or two ($C_1$–$C_3$) alkyl radicals, phenyl which is optionally substituted by one or two ($C_1$–$C_3$) alkyl radicals.

2. A germoxane of formula II according to claim 1, wherein n is an integer lower than 6.

3. A germoxane of formula II according to claim 1, wherein $R_3$, $R_4$ are chosen among the phenyl optionally substituted by one or two ($C_1$–$C_3$) alkyl radicals.

4. A germoxane of formula II according to claim 1, wherein $R_3$, $R_4$ together form a divalent chain —C—C=C—C— which is optionally substituted by 1 or 2 methyl or ethyl substituents, but on two different carbons.

5. A germoxane of formula II according to claim 1, wherein $R_5$ is an n-propyl or n-butyl radical.

6. A germoxane of formula II according to claim 1:

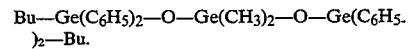
Bu—Ge(C$_6$H$_5$)$_2$—O—Ge(CH$_3$)$_2$—O—Ge(C$_6$H$_5$)$_2$—Bu.

7. A germoxane of the formula:

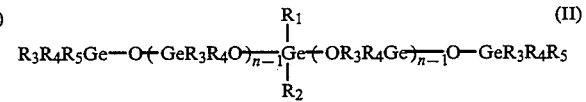

wherein n is an integer between 1 and 50, $R_1$, $R_2$ are chosen among the phenyl optionally substituted by one to five ($C_1$–$C_3$) alkyl radicals $R_3$, $R_4$, $R_5$ are chosen among the radicals ($C_1$–$C_{12}$) alkyl, ($C_2$–$C_{12}$) alkenyl, ($C_3$–$C_6$) cycloalkyl which is optionally substituted by one or two ($C_1$–$C_3$) alkyl radicals, phenyl which is optionally substituted by one to five ($C_1$–$C_3$) alkyl radicals.

8. A germoxane of formula II according to claim 7 wherein n is an integer lower than 6.

9. A germoxane of formula II according to claim 7 wherein $R_1$, $R_2$ are chosen among the phenyl trisubstituted.

10. A germoxane of formula II according to claim 7 wherein $R_1$, $R_2$ are chosen among the phenyl trimethyl substituted.

11. A germoxane of formula II according to claim 7, wherein $R_1$, $R_2$ are -o, -o, -p phenyl trimethyl substituted.

12. A germoxane of formula II according to claim 7, wherein $R_3$, $R_4$, $R_5$ are chosen among the ($C_1$-$C_6$) alkyl radicals, ($C_2$-$C_6$) alkenyle radicals.

13. A germoxane of formula II according to claim 7, wherein $R_3$, $R_4$, $R_5$ are chosen among the methyl or ethyl radicals.

14. A germoxane of the formula 2:

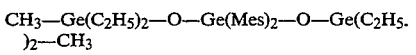

wherein Mes is O—, O—, p—, $C_6H_2$ $(CH_3)_3$.

* * * * *